United States Patent
Rudert

(10) Patent No.: US 8,284,396 B2
(45) Date of Patent: Oct. 9, 2012

(54) SYSTEM AND DEVICE FOR THE OPTICAL INSPECTION OF GLASS PANELS

(75) Inventor: Armin Rudert, Essen (DE)

(73) Assignee: Isra Vision AG, Darmstadt (DE)

( * ) Notice: Subject to any disclaimer, the term of this patent is extended or adjusted under 35 U.S.C. 154(b) by 30 days.

(21) Appl. No.: 12/090,903

(22) PCT Filed: Oct. 17, 2006

(86) PCT No.: PCT/EP2006/010007
§ 371 (c)(1),
(2), (4) Date: Jul. 8, 2008

(87) PCT Pub. No.: WO2007/045437
PCT Pub. Date: Apr. 26, 2007

(65) Prior Publication Data
US 2008/0316476 A1    Dec. 25, 2008

(30) Foreign Application Priority Data
Oct. 21, 2005 (DE) .......................... 10 2005 050 882

(51) Int. Cl.
*G01N 21/958* (2006.01)
(52) U.S. Cl. ................................. 356/239.1; 356/239.7
(58) Field of Classification Search ............... 356/239.1, 356/239.4, 239.7, 239.8, 237.1–237.5; 250/223 B, 250/223 R
See application file for complete search history.

(56) References Cited

U.S. PATENT DOCUMENTS

| | | | |
|---|---|---|---|
| 5,128,550 A | 7/1992 | Erbeck | |
| 5,220,178 A * | 6/1993 | Dreiling et al. | 250/559.03 |
| 5,309,222 A | 5/1994 | Kamei et al. | |
| 5,387,978 A | 2/1995 | Okafuji et al. | |
| 5,459,330 A * | 10/1995 | Venaille et al. | 250/559.45 |
| 5,642,198 A | 6/1997 | Long | |
| 5,917,602 A * | 6/1999 | Bonewitz et al. | 356/614 |
| 6,031,221 A * | 2/2000 | Furnas | 250/223 B |
| 6,501,546 B1 * | 12/2002 | Weiss | 356/239.1 |
| 6,512,239 B1 | 1/2003 | Weiss et al. | |
| 6,618,136 B1 * | 9/2003 | Ishida | 356/239.1 |
| 6,633,377 B1 | 10/2003 | Weiss et al. | |
| 7,369,240 B1 * | 5/2008 | Abbott et al. | 356/429 |
| 7,567,344 B2 * | 7/2009 | LeBlanc et al. | 356/239.1 |
| 2008/0062422 A1 * | 3/2008 | Thomas et al. | 356/432 |
| 2008/0278718 A1 * | 11/2008 | Sonda | 356/239.8 |
| 2010/0051834 A1 * | 3/2010 | Lopatin | 250/553 |

FOREIGN PATENT DOCUMENTS

DE    24 27 054    1/1975
(Continued)

*Primary Examiner* — Hoa Pham
(74) *Attorney, Agent, or Firm* — Michael J. Striker

(57) ABSTRACT

A system for the optical inspection of glass panels (2) is described, with a conveying device (3) for moving a glass panel (2), and with a first inspection module (5, 6, 7), which includes an illumination device and a camera for illuminating and photographing the glass panel (2), and with a first evaluation module (8, 9, 10, 11) for evaluating the photographs of the glass panel (2). In addition, a second inspection module (5, 6, 7) is provided, which includes an illumination device or a camera for illuminating the photograph of the glass panel (2), and it is connected with a second evaluation module (8, 9, 10, 11) for evaluating the photographs taken of the glass panel, the illumination systems and/or the cameras of the first inspection module (5, 6, 7) and the second inspection module (5, 6, 7) having different designs and/or being located in different places relative to the glass panel (2), which is moved past the inspection modules (5, 6, 7) via the conveying device. The present invention also relates to a method carried out using this system (1).

18 Claims, 3 Drawing Sheets

FOREIGN PATENT DOCUMENTS

Figure 1:
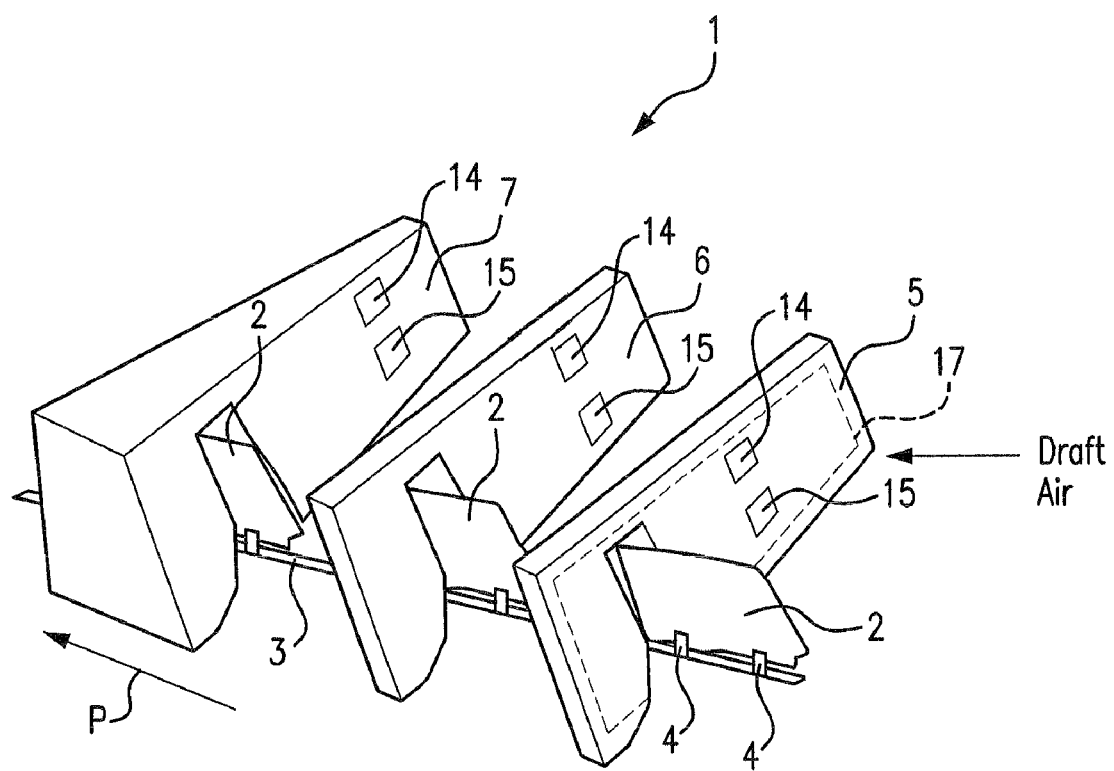

| | | |
|---|---|---|
| DE | 31 08 234 | 9/1982 |
| EP | 0 416 302 | 3/1991 |
| GB | 1 432 120 | 4/1976 |
| JP | 2-052149 | 4/1990 |
| JP | 5-249052 | 9/1993 |
| JP | 6-148100 | 5/1994 |
| JP | 8-327561 | 12/1996 |
| JP | 10-176995 | 6/1998 |
| WO | 98/34096 | 8/1998 |

* cited by examiner

SYSTEM AND DEVICE FOR THE OPTICAL INSPECTION OF GLASS PANELS

The present invention relates to a system and a device for the optical inspection of glass panels. A conveying device for moving the glass panels, and an inspection module are provided for this purpose. The inspection module includes an illumination device and a camera for illuminating and photographing the glass panels, and it is connected with an evaluation module for evaluating the photographs of the glass panels. The present invention is suited, in particular, for use in inspecting bent or curved glass panels, e.g., which will be installed in an automobile.

In industrial processes that involve glass panels, e.g., windshields or other types of automotive windows, it is necessary to inspect the quality of the panels after production and before they are installed in the chassis. Various methods and systems designed for this purpose are known, which are capable, e.g., of detecting optical flaws in large-surface panels, ascertaining the imaging characteristics of the glass panels, measuring the thickness of a panel, or detecting scratches or other flaws in the glass panels. These proposed systems and methods typically require special illumination and photographing systems, so that the particular detection task desired may be performed in an optimal manner. The photography conditions that are optimal for detecting the type of flaw are usually not suited for ascertaining other types of flaws or properties of the glass panel, however. It has therefore not been possible to determine and display the optical characteristics of a panel and the quality of production in one system.

The object of the present invention, therefore, is to provide a method for the optical inspection of glass panels that may perform an overall evaluation of the optical characteristics and quality of a glass panel after production using a simple method that may be flexibly adapted to the particular production conditions. This object is achieved via the features of independent claims 1 and 12.

With a system for the optical inspection of glass panels, a first inspection module is provided—as is a second inspection module—with an illumination device and a camera for illuminating and photographing the glass panel. Similar to the first inspection module, the second inspection module is connected with a second evaluation module for evaluating the photographs of the glass panel. The illumination devices and/or the cameras of the first inspection module and the second inspection module have different designs, and/or they are located in different places relative to the glass panel, which is moved past the inspection modules via the conveying device.

By locating several different inspection modules on a conveying device for moving the glass panels, it is attained according to the present invention that various measurements of a glass panel may be carried out in a coordinated manner, using a single compact system. In contrast to a configuration of several separate monitoring or control systems, each of which delivers a single measured result, it is therefore possible using the proposed system—by combining various inspection modules in one system—to combine the measured results from various inspection modules with each other and to combine the results of the individual evaluations in such a manner that an inspection result is automatically generated as a complete report on the entire test specimen. In addition to compiling the results from the individual inspection modules, the inventive interaction of the several inspection modules also results in an overall improvement of the inspection result, because the results from one inspection module may be taken into account in the result from another inspection module. In addition, the interaction of various inspection modules in one single system reduces the total number of system components required, since certain sub-measurements must be carried out for each inspection system and/or method, which therefore need be carried out only once in the inventive system. In addition to the cost savings associated therewith, the proposed system is also capable of generating a complete inspection result of a glass panel particularly quickly, and it may therefore be used particularly close to the production process. It may be easily incorporated in the production sequence without having to stop or slow down production in order to perform the inspection.

For the combined evaluation of individual inspection results in the overall system, it is particularly advantageous when a central evaluation unit is provided that is installed downstream of the evaluation modules assigned to the individual inspection modules. Given that an independent evaluation module is preferably assigned to each inspection module, the evaluation of the photographs taken by the inspection module may start as soon as the photograph is taken, thereby preventing delays in this step, while the inspection modules—which are installed one after the other—perform inspections in parallel of the glass panel, which is moved past the inspection modules using the conveying device. It is provided according to the present invention that reference triggers are located on the conveying device, in order to easily cross-reference the locations of the defects identified via the inspection modules. It is also possible, as an alternative, to determine the location of defects via design data on the glass panel stored in the system, and via a two- and three-dimensional position measurement of the glass panel in each inspection module. The latter method has the advantage that the location of the defect is not known relative to the conveying device located outside of the glass panel, but rather within the coordinate system of the glass panel itself. As a result, the inspection could therefore be performed at different conveyor belts. The amount of measurement effort required would be greater, however.

An inspection that is optimal and complete in terms of the information made available regarding the optical characteristics and typical defects in a glass panel may be attained according to the present invention by providing at least three inspection modules, each of which includes at least one evaluation module assigned thereto.

Of the three inspection modules in all, the system preferably includes a module with raster illumination and a transmission system. In a module of this type, a light source of the illumination device projects a defined pattern of regular sequences through the glass panel and onto the camera. The sequences have at least two different light intensities, and the raster boundaries of the projected image are preferably depicted on a specified number of camera pixels. If the optical imaging properties of the glass panel are not optimal, or if they are flawed, the projected pattern is reproduced in the camera image in a less-than-optimal manner. Depending on the type of depiction, it is possible to deduce what the flaws are in the optical imaging properties. With this method, it is also possible for a moiré pattern to appear on the camera pixels, which is detectable as a phase shift at the output of the camera pixels. The angle by which the light beam was deflected may be easily determined. The optical power of the panel may be determined in this manner, for example. In this inspection module, an inspection for flaws in the transmission optics of the glass panel is therefore carried out.

According to the present invention, and particularly advantageously, a module with a transmitted-light system is provided as another one of the three inspection modules, and which is used in particular to inspect for absorbing defects.

With this design, the glass panel is illuminated by the most homogeneous light source possible, in particular, and the transmission differences are determined using a camera. This module with a transmitted-light system is also particularly suited for identifying flaws in printing using a camera, since the panel—which is otherwise light when illuminated—must turn dark in the area where the printing is located. If light points appear in the areas that should be dark due to printing, then the printing is not optimal or it is flawed at this point. This method is also suited for use in determining, e.g., the thickness of the print layer that was applied, and for determining fluctuations in the layer thickness of the printing, using an intensity measurement.

A further inspection module, which is preferably provided with a three-modular design of the system, is a module with a system for detecting scratches. A system of this type photographs, and detects a scan line on the material surface of the glass panel. Therein, an illumination device preferably generates parallel light that is transverse to a direction of the scan line and that is diffuse or quasi-diffuse in the direction of the scan line. Preferably, a further illumination device generates diffuse or quasi-diffuse light transverse to the scan line is provided. A camera that photographs, and detects the scan line is preferably oriented such that the recording area of the camera points into the light trap. Due to the scattering of light, any scratches, air bubbles, or other flaws in the glass panel produce a well-contrasted image of the flaw in the dark image of the light trap, which may then be easily measured and classified.

Even though the three aforementioned inspection modules are provided, particularly advantageously, in a design of a system with three inspection modules, in order to obtain the most comprehensive information possible about the test specimen, it is not absolutely necessary according to the present invention to always provide these three modules in a system used to inspect for flaws. It is also possible, e.g., to eliminate modules and/or to replace them with other modules, depending on the purpose of the inspection.

A further inspection module that is suitable for use in conjunction with the present invention is a module with raster illumination and a reflectance system, with which a raster projected onto the glass panel is therefore measured in a reflecting configuration. Flaws in the reflectance optics of the glass may be identified in this manner. Furthermore, a module for measuring the shape of the panel may be provided, which includes, e.g., cameras that also detect the panel edge of the image in particular, and that determine the shape of the panel by evaluating the edge of the panel. A module of this type could also be used to inspect for flaws on the edges. The module with transmitted-light systems may also be suitable for use in evaluating flaws on the edges by performing a separate evaluation of the images of the panel edge. The same applies for measuring a course of the panel edge. To measure the shape of the panel, the curvature or thickness of bent glass panels may also be determined, for example. To this end, the inspection module may include at least one laser beam as the illumination device, the laser beam being divided via suitable beam optics into a total of two or three laser beams, two of which strike the glass panel next to each other at different angles of incidence. A third laser beam is produced from one of the two laser beams, with parallel displacement. The reflectance of the laser beams on the front and rear boundary surface of the glass is detected using suitable cameras. Via the incident light beams that strike the glass surface at different angles, it is possible to determine the thickness of the specimen and to perform a correction of the angle of inclination or the wedge angle. The curvature may be corrected based on the third laser beam, which is parallel to the first or second laser beam. A further possibility for measuring the panel shape is to depict a basically sinusoidal pattern on a camera after it is reflected on the glass panel or after it passes through the glass panel, and to determine the local phase of this pattern in the plane of the image. This method may also be used to make deductions about the shape of the glass panel. In this case, the module for measuring the shape of the panel includes a suitable pattern-generation device as the illumination device.

According to the present invention, in one inspection module, and particularly the inspection module with the transmitted-light system, at least one additional camera may be provided in the dark field, which is not reached by the illumination device of the inspection module. This inspection module may be used, in particular, to inspect for edge flaws and/or to measure the shape of the panel.

In conjunction with the measurement of the panel shape in particular, cameras may also be installed in a stereo configuration in a module with a transmitted-light system or in a module for measuring the panel shape, in order to perform a three-dimensional measurement of the panel edge, for instance. By using stereo cameras in an inspection module in this manner, it is possible to measure the position and shape of the edge three-dimensionally as well, with particular accuracy.

According to a particularly preferred embodiment of the inventive method, an inspection module, several inspection modules, or all inspection modules of the system are set up to measure the glass panel as it passes by, e.g., as it moves. A continual inspection process during on-going production is thereby made possible. This may be attained, e.g., by using a sufficiently great contrast and correspondingly short illumination times of the cameras.

A preferred application of the system and method for the optical inspection of glass panels involves automotive glass panels, e.g., windshields, rear windows, and side windows. The present invention is equally suitable for use, in particular, with bent and/or curved glass panels.

According to the present invention, it may also be provided that, in one inspection module, the camera is positioned at a slant relative to the glass panel, and in another inspection module, the camera is positioned perpendicularly to the glass panel. This makes it possible, depending on how the glass panel is installed, to inspect particulary important viewing directions through the glass panel in an automated manner and using the same system.

Every inspection module is preferably designed as a separate unit, with the several inspection modules being located one after the other in the direction of conveyance. Via this modular design of the inventive system, the inspection system may be adapted particularly easily to different inspection tasks, e.g., for various types of production, without having to de-install and readjust the entire system. The evaluation module that is specially assigned to this inspection module may also be integrated in each inspection module. The results of this evaluation module may then be sent in a standardized manner to the central evaluation unit for the further, higher-order evaluation.

To minimize the disturbances that occur when an inspection module is measured, an inspection module may be shielded against incident light and/or the inflow of draft air.

With the inventive method for the optical inspection of glass panels, which is carried out in particular using the system described above, a glass panel is moved past a first inspection module, the glass panel is illuminated and photographs are taken of it, and these photographs are evaluated using a first evaluation method in a first evaluation module.

According to the present invention, the glass panel is then moved past at least a second evaluation module. The glass panel is illuminated and photographs are taken with a camera. These photographs are evaluated in a second evaluation module using a second evaluation method, which differs from the first evaluation method. Via the combination of several different evaluation methods and configurations, a comprehensive inspection of all or many characteristics of the glass panel under investigation is attained according to the present invention.

An essentially complete inspection of the glass panel may be attained by moving the glass panel past at least three inspection modules and by using at least three evaluation methods. The inspection modules are preferably a module with raster illumination, a module with a transmitted-light system, and a module with a system for scratch detection. The following inspections are carried out in the particular modules: An inspection for flaws in the optics of the glass panel, an inspection for absorbing defects, and an inspection for scratches. If the glass panel has been printed on, it may also be inspected for printing errors.

Depending on the requirements desired, by using the inventive method and/or in addition to the aforementioned evaluation method, it is possible to perform an inspection for edge defects, and/or to measure the panel shape and/or the course of the panel shape.

According to an advantageous embodiment of the present invention, it is provided that non-inspected regions of the glass panel are recognized when the images are processed in an evaluation method, based on specified criteria. As a result, any error messages that may have occurred otherwise are suppressed.

According to the present invention, the glass panels may be photographed while the glass panel moves past the inspection module, i.e., while it is in motion.

To obtain a comprehensive, overall inspection result, the results of the various evaluation methods may be combined in one central evaluation unit.

The results of the various evaluation methods may be linked with each other according to the present invention, and a higher-order evaluation may be carried out using the results from several inspection units. It is therefore also possible, in particular, to link the various results from the various inspection modules with each other, and to thereby obtain a more precise inspection result overall.

According to the present invention, it is therefore possible to obtain a complete, overall evaluation of the glass panel based on the results from all inspection modules, and to display it in the form of a report or a visual depiction.

Further features, advantages, or potential applications of the present invention also result from the following description of an exemplary embodiment, and from the drawing. All of the described and/or graphically depicted features are part of the present invention, either alone or in any combination, independently of their wording in the claims or their back-references.

Figure 1A:
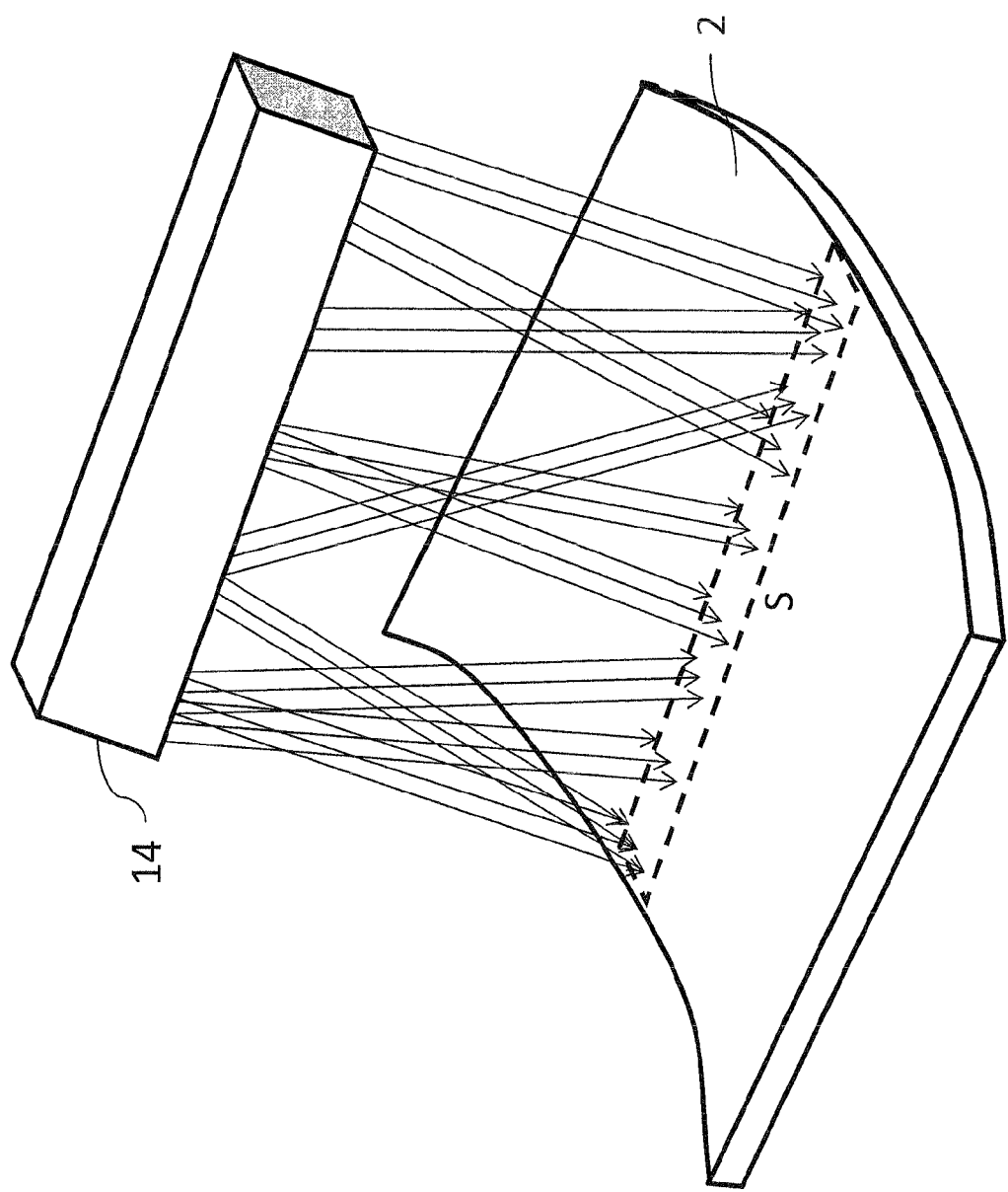
Figure 2:
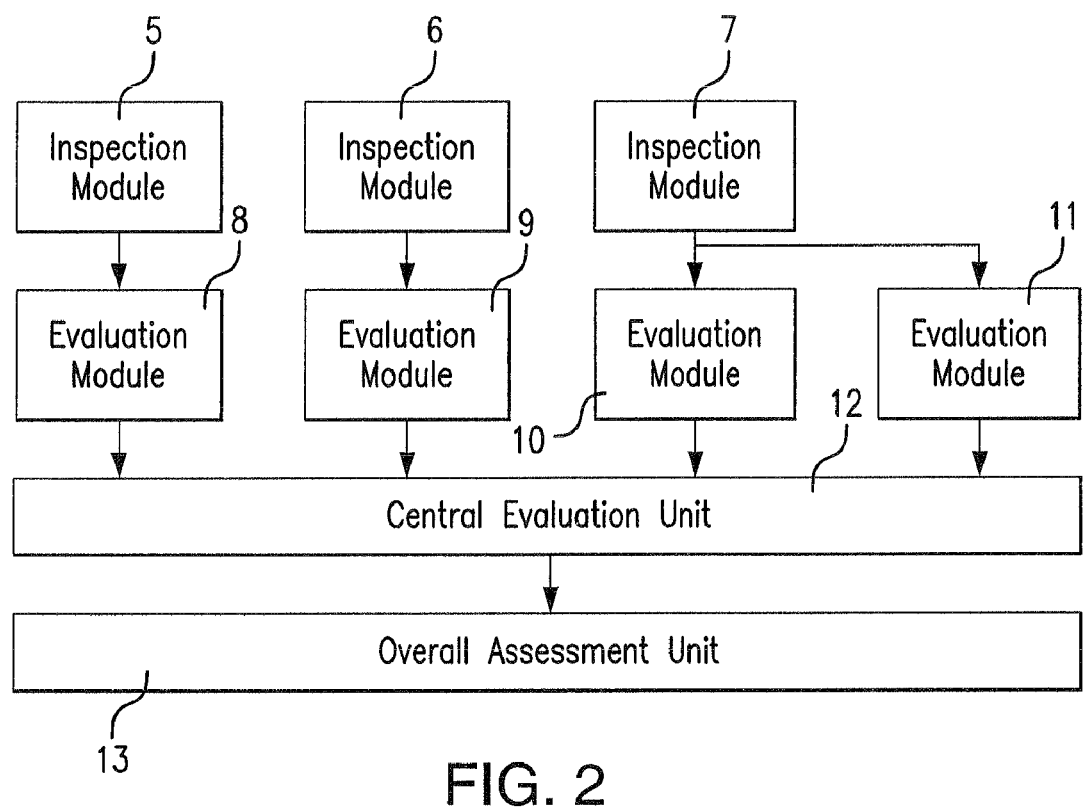

FIG. 1 is a schematic overall view of an inventive system for the optical inspection of glass panels, with three inspection modules, FIG. 1A depicts an illumination device illuminating a glass panel, and FIG. 2 is a block diagram that illustrates how the inventive method is carried out.

System 1 for the optical inspection of glass panels 2 shown in FIG. 1 is located on a conveyor belt 3, which is designed as a conveying device, and on which glass panels 2 are retained using suitable holders 4. System 1 includes several inspection modules 5, 6, 7, which are located on conveyor belt 3 such that they enclose glass panels 2 to be inspected while they pass through system 1 for optical inspection on conveyor belt 3 in the direction of arrow P.

According to the present invention, first inspection module 5 is a module with raster illumination and a transmission system, in which an inspection for flaws in the transmission optics of glass panel 2 takes place, in order to determine an optical distortion. When the preferred inspection of windshields for automotive vehicles is carried out with system 1, glass panels 2 are typically inspected in the viewing direction, in which the driver looks through glass panel 2 when it is installed. With a windshield, this is at an angle of approximately 60° to the glass panel normal. Using moiré technology, imaging errors in the vertical and horizontal direction are detected in inspection module 5.

Second inspection module 6, through which glass panel 2 to be inspected passes, is a module for scratch detection, with which flaws such as scratches, air inclusions, or chips in the glass are detected via light scattering. To this end, the light scattered by the surface of glass panel 2 to be inspected is detected and analyzed. The magnitude of the mechanical flaw, the effects on light scattering, and the position of the flaw are detected. This information is then used to classify and locate the flaws. For the inspection, glass panel 2 is preferably illuminated with light generated parallel to and perpendicularly to a scan line of the camera. The camera looks through the scan line on glass panel 2 and into a light trap. When glass panel 2 is intact, a dark image is therefore registered. Via the light, which is oriented in mutually orthogonal directions, scattering therefore takes place when there are scratches or flaws in glass panel 2. This scattering is easily detected by the camera located in front of the dark background of the light trap. Inspection module 6 also inspects the edges of the glass panel for scratches. FIG. 1A shows a glass panel 2 with a scan line (S) extending between a top and a bottom material surface illuminated by, light from an elongated illumination device 14. The combined light as shown is both parallel in a direction transverse to the scan line (S) and diffuse or quasi-diffuse in a longitudinal direction aligned with the scan line (S). The elongated illumination device 14 is readily arranged within any of inspection modules 5, 6, 7.

The last of the three inspection modules is a module 7 with a transmitted-light system, which is used to inspect for absorbing defects. Using appropriate transmission measurements, defects caused by inclusions in the glass and printing errors may be identified.

Inspection modules 5, 6, and 7 are cladded, in order to protect the measuring systems from scattered light and drafts, and to ensure that the measuring systems are reliable.

The inspections carried out in the individual inspection modules 5, 6 and 7 are evaluated in separate evaluation modules 8, 9, 10 and 11, which are not shown in FIG. 1, and which may be integrated in the housing of inspection modules 5, 6, 7, or which may be designed separately, e.g., as a PC.

An illumination device 14 and a camera 15 are shown in FIG. 1 within each of inspection modules 5, 6 and 7. In an embodiment, the illumination device 14 and camera 15 of an inspection module operate as raster illumination and reflectance systems, respectively. In an embodiment, an inspection module 6 includes that the illumination device 14 is a transmitted-light system, and an additional camera 15 is included to operate in the dark field. The reader should note that camera 14 within inspection module 5 is positioned at a slant with respect to the glass panel 2, and that camera 15 within inspection module 7 is positioned perpendicular to the glass panel 2.

A shield 17 is shown included within inspection module 5, as well as an arrow identified with the phrase "Draft Air" to make clear that the shield 17 protects the module from incident light or an inflow of draft air.

In system 1, the inspection therefore takes place in several separate inspection modules 5, 6, 7, which are installed one after the other. Each of these modules 5, 6, 7 realizes a configuration—which is adapted to the inspection method—of glass panel 2 to be inspected, and they realize the camera and illumination provided in the inspection modules. Modules 5, 6, 7 are designed such that glass panels 2 on conveyor belt 3 may pass through individual modules 5, 6, and 7 one after the other without their having to be removed from conveyor belt 3, and without the need to halt conveyor belt 3.

The method for performing the inspection will be described in greater detail below with reference to the block diagram in FIG. 2.

The starting point of the inspection are the measurements in inspection module 5 with raster illumination and a transmission system, inspection module 6 for scratch detection, and inspection module 7 with a transmitted-light system, for the purposes of which photographs of glass panel 2 are taken with cameras. These photographs are sent to one or more separate evaluation modules 8, 9, 10, 11 for each inspection module 5, 6, 7, in which the photographs are evaluated using an appropriate evaluation method.

The photographs from inspection module 5 are sent to evaluation module 8 for inspection for defects in the transmission optics. The photographs from inspection module 6 are evaluated in evaluation module 9 to inspect for scratches.

The photographs of inspection module 7 with the transmitted-light system are sent in parallel to evaluation module 10 for inspection for absorbing defects, and they are sent to evaluation module 11 for inspection for printing errors. Since the evaluation of photographs carried out to identify printing errors and other absorption errors is based on different evaluation methods, it makes sense to perform this evaluation in parallel, in order to attain a rapid inspection, which may be carried out on-line as part of the production process.

In a first method step, the defects in a glass panel 2 are initially identified separately in each of the inspection modules 5, 8, 7, and their features (type of defect, position, or the like) are determined and/or measured. These individual pieces of information are compiled in a central evaluation unit 12. Using the information from all evaluation modules 8 through 11, it is possible to perform a reliable error classification, since a wide variety of information is available on each defect due to the fact that inspection modules 5, 6, and 8 are connected one behind the other, and they are combined with the evaluation results in evaluation modules 8, 9, 10, 11.

The use of inspection modules 5, 6, 7 described above, with raster illumination and a transmission system, for scratch detection, and with a transmitted-light system for evaluating the inspection for defects in the transmission optics, i.e., to identify scratches, absorbing defects, and possible printing errors is a reasonable combination of inspection methods, because they ensure that all variables of interest in the process to manufacture a glass panel are determined and that the most important faults are found, since all essential fault effects and dimensions—except for the panel shape—are determined. Determining the shape of the panel is usually more complex, and it is therefore often measured in a different stage of production. According to the present invention, it is immediately possible, however, to also integrate a module for measuring the panel shape in the system.

Inspection modules 5, 7 with raster illumination and a transmitted-light system with the related evaluation method used to inspect for flaws in the transmission optics and for absorbing defects are an ideal combination, since it is difficult to identify absorbing faults in inspection module 5 using a system of camera and illumination unit that measures the optics, and it is not possible to determine the optical characteristics using a configuration of camera and illuminating unit in inspection module 7 for the transmitted-light system. The same applies for module 6, which is used to detect scratches, because scratches may disturb the measurement of the optical characteristics, even though they are not always detected using the configuration per 1. By connecting inspection modules 5, 6 and 7 one after the other, it is therefore possible to link all important information together and to perform a higher-order evaluation, in which the information from individual inspection modules 5, 6, and 7 may be linked in a technically reasonable manner.

Evaluation modules 8, 9, 10 and 11 represent the first stage of an evaluation computer system that is designed such that inspection modules 5, 6 and 7, and the inspection evaluations in evaluation modules 8, 9, 10 and 11 may be combined in any possible manner. The present invention is therefore not limited to the embodiment shown, with special inspection modules 5, 6, 7 and evaluation modules 8, 9, 10 and 11. Instead, it may be adapted to different inspection tasks in any possible manner.

In a final method step, an overall evaluation 13 of glass panel 2 is performed, which uses all of the information from the different inspection modules 5, 6, 7. This includes a fault report and definitive information about the optical characteristics of glass panel 2. All variables and faults that are interesting to a manufacturer of glass panels may therefore be captured and displayed in compact system 1. In a preferred depiction of the overall evaluation, the image of a panel may be shown on a display, in which the optical characteristics of glass panel 2 are depicted, e.g., using a false-color illustration, and the flaws that were found are indicated, with a different symbol being used for the different fault classifications.

Inventive system 1 and/or the method carried out with this system is therefore capable of performing a complete inspection of a glass panel 2 using a single system, and of displaying all important data regarding the production and quality of glass panel 2.

REFERENCE NUMERALS

1 System for the optical inspection of glass panels
2 Glass panel
3 Conveying device, conveyor belt
4 Holder
5 Inspection module with raster illumination and transmission system
6 Inspection module for detecting scratches
7 Inspection module with transmitted-light system
8 Evaluation module for inspecting for defects in the transmission optics
9 Evaluation module for inspecting for scratches
10 Evaluation module for inspecting for absorbing defects
11 Evaluation module for inspecting for printing errors
12 Central evaluation unit
13 Overall assessment
14 illumination device 15 camera
17 shield
P Direction of conveyance

What is claimed is:

1. A system for the optical inspection of glass panels, with a conveying device for moving the glass panel, and with a first inspection module, which includes an illumination device and a camera for illuminating and photographing the glass panel, and which is connected with a first evaluation module for evaluating the photographs of the glass panel, characterized by at least a second inspection module with an illumination device and a camera for illuminating and photographing the glass panel, which is connected with a second evaluation module for evaluating the photographs of the glass panel, the illumination devices or the cameras of the first inspection module and the second inspection module having different designs or being located in different places relative to the glass panel, which is moved past the inspection modules via the conveying device in a conveying direction; wherein the inspection modules are designed as separate units that are located one after the other along the conveying direction and wherein one of the inspection modules operates as a scratch detection system, wherein the scratch detection system is configured such that the illumination device for illuminating the glass panel therein generates light that is both parallel in a direction transverse to a scan line included on a material surface of the glass panel and diffuse or quasi-diffuse in a direction aligned with the scan line, and wherein a central evaluation unit compiles results derived from evaluation of the photographs of the glass panel by the first and second evaluation units.

2. The system as recited in claim 1, characterized by a central evaluation unit, which is connected downstream of the evaluation modules.

3. The system as recited in claim 1, wherein at least three inspection modules are provided, each of which includes an assigned evaluation module.

4. The system as recited in claim 1, wherein the inspection modules of the system are modules of the group consisting of a raster illumination and a reflectance system module, a transmitted-light system module, a scratch detection system module and panel shape measuring module.

5. The system as recited in claim 1, wherein in one inspection module, at least one camera is provided in the dark field that is not reached by the illumination device of the inspection module.

6. The system as recited in claim 1, wherein in one inspection module, cameras are mounted in a stereo configuration.

7. The system as recited in claim 1, wherein one, more, or all inspection modules of the system are set up to measure the glass panel as it passes by.

8. The system as recited in claim 1, wherein the glass panel is an automotive glass panel.

9. The system as recited in claim 1, wherein, in one inspection module, the camera is positioned at a slant relative to the glass panel and in another inspection module, the camera is positioned perpendicularly to the glass panel.

10. The system as recited in claim 1, wherein one inspection module is shielded against incident light or the inflow of draft air.

11. A method for the optical inspection of glass panels, in particular using the system as recited in claim 1, with which a glass panel is moved past a first inspection module, during which time the glass panel is illuminated and photographed using a camera, and these photographs are evaluated using a first evaluation method in a first evaluation module, wherein the glass panel is then moved past at least a second inspection module, during which time the glass panel is illuminated and photographed using a camera, and these photographs are evaluated using a second evaluation method, which differs from the first evaluation method, in a second evaluation module.

12. The method as recited in claim 11, wherein the glass panel is moved past at least three inspection modules, and at least three evaluation methods are used.

13. The method as recited in claim 11, wherein the photographs taken by one inspection unit are evaluated using several evaluation methods.

14. The method as recited in claim 11, wherein the evaluation method used is an inspection for optical defects in the glass panel in transmission or reflectance optics, an inspection for absorbing defects, an inspection for scratches, an inspection for edge defects or a measurement of the panel shape or the course of the panel shape.

15. The method as recited in claim 11, wherein non-inspected regions of the glass panel are recognized when the images are processed in an evaluation method, based on specified criteria.

16. The method as recited in claim 11, wherein the glass panels are photographed as they pass by the inspection module.

17. The method as recited in claim 11, wherein the results of the various evaluation methods are linked, and a higher-order evaluation is performed based on the results obtained by several inspection modules.

18. The method as recited in claim 11, wherein a complete, overall assessment of the glass panel is determined based on the results from all inspection modules, and it is displayed.

\* \* \* \* \*